United States Patent
Jones et al.

(10) Patent No.: US 8,778,007 B2
(45) Date of Patent: Jul. 15, 2014

(54) SYSTEMS FOR PERFORMING INTRALUMENAL RECONSTRUCTION

(75) Inventors: Donald K. Jones, Dripping Springs, TX (US); Vladimir Mitelberg, Austin, TX (US)

(73) Assignee: Empirilon Technology, LLC, Dripping Springs, TX (US)

( * ) Notice: Subject to any disclaimer, the term of this patent is extended or adjusted under 35 U.S.C. 154(b) by 53 days.

(21) Appl. No.: 13/533,872

(22) Filed: Jun. 26, 2012

(65) Prior Publication Data

US 2012/0265288 A1 Oct. 18, 2012

Related U.S. Application Data

(63) Continuation-in-part of application No. PCT/US2011/022255, filed on Jan. 24, 2011.

(60) Provisional application No. 61/501,732, filed on Jun. 27, 2011, provisional application No. 61/501,736, filed on Jun. 27, 2011, provisional application No. 61/501,738, filed on Jun. 27, 2011, provisional application No. 61/298,046, filed on Jan. 25, 2010, provisional application No. 61/298,060, filed on Jan. 25, 2010.

(51) Int. Cl.
*A61F 2/06* (2013.01)
*A61F 2/88* (2006.01)
*A61F 2/966* (2013.01)
*A61F 2/82* (2013.01)
*A61F 2/91* (2013.01)

(52) U.S. Cl.
CPC . *A61F 2/88* (2013.01); *A61F 2/966* (2013.01); *A61F 2002/823* (2013.01); *A61F 2/91* (2013.01)
USPC .................................................. 623/1.11

(58) Field of Classification Search
USPC ........... 604/103.05, 103.07, 103.14; 606/194, 606/191, 192, 198, 108, 195, 159, 200; 623/1.11–1.18, 1.2, 1.22
See application file for complete search history.

(56) References Cited

U.S. PATENT DOCUMENTS

| | | | | |
|---|---|---|---|---|
| 4,271,839 A * | 6/1981 | Fogarty et al. | ................ | 606/194 |
| 5,662,703 A * | 9/1997 | Yurek et al. | .................. | 623/1.12 |
| 7,947,071 B2 * | 5/2011 | Schmid et al. | .............. | 623/1.22 |
| 8,016,872 B2 * | 9/2011 | Parker | .......................... | 623/1.11 |
| 2002/0095114 A1 * | 7/2002 | Palasis | ....................... | 604/96.01 |
| 2004/0006380 A1 * | 1/2004 | Buck et al. | ................... | 623/1.11 |

* cited by examiner

*Primary Examiner* — Kathleen Holwerda
*Assistant Examiner* — Jocelin Tanner
(74) *Attorney, Agent, or Firm* — Donald K. Jones (57) ABSTRACT

Devices, systems and methods are provided for performing intra-lumenal medical procedures in a desired area of the body. Stents, stent delivery devices and methods of performing medical procedures to redirect and or re-establish the intravascular flow of blood are provided for the treatment of hemorrhagic and ischemic disease states.

10 Claims, 9 Drawing Sheets

SYSTEMS FOR PERFORMING INTRALUMENAL RECONSTRUCTION

CROSS-REFERENCE TO RELATED APPLICATIONS

This application claims the benefit of U.S. Provisional Application No. 61/501,732 filed Jun. 27, 2011, U.S. Provisional Application No. 61/501,736 filed Jun. 27, 2011 and U.S. Provisional Application No. 61/501,738 filed Jun. 27, 2011 all of which are hereby incorporated by reference herein in their entireties.

This application is a continuation in part of International Application No. PCT/US2011/022255 filed Jan. 24, 2011, which claims the benefit of U.S. Provisional Application No. 61/298,046 filed Jan. 25, 2010 and U.S. Provisional Application No. 61/298,060 filed Jan. 25, 2010 all of which are hereby incorporated by reference herein in their entireties.

BACKGROUND OF THE INVENTION

The field of intralumenal therapy for the treatment of vascular disease states has for many years focused on the use of many different types of therapeutic devices. While it is currently unforeseeable that one particular device will be suitable to treat all types of vascular disease states it may however be possible to reduce the number of devices used for some disease states while at the same time improve patient outcomes at a reduced cost. To identify potential opportunities to improve the efficiency and efficacy of the devices and procedures it is important for one to understand the state of the art relative to some of the more common disease states.

For instance, one aspect of cerebrovascular disease in which the wall of a blood vessel becomes weakened. Under cerebral flow conditions the weakened vessel wall forms a bulge or aneurysm which can lead to symptomatic neurological deficits or ultimately a hemorrhagic stroke when ruptured. Once diagnosed a small number of these aneurysms are treatable from an endovascular approach using various embolization devices. These embolization devices include detachable balloons, coils, polymerizing liquids, gels, foams, stents and combinations thereof.

The most widely used embolization devices are detachable embolization coils. These coils are generally made from biologically inert platinum alloys. To treat an aneurysm, the coils are navigated to the treatment site under fluoroscopic visualization and carefully positioned within the dome of an aneurysm using sophisticated, expensive delivery systems. Typical procedures require the positioning and deployment of multiple embolization coils which are then packed to a sufficient density as to provide a mechanical impediment to flow impingement on the fragile diseased vessel wall. Some of these bare embolization coil systems have been describe in U.S. Pat. No. 5,108,407 to Geremia, et al., entitled, "Method And Apparatus For Placement Of An Embolic Coil" and U.S. Pat. No. 5,122,136 to Guglielmi, et al., entitled, "Endovascular Electrolytically Detachable Guidewire Tip For The Electroformation Of Thrombus In Arteries, Veins, Aneurysms, Vascular Malformations And Arteriovenous Fistulas." These patents disclose devices for delivering embolic coils at predetermined positions within vessels of the human body in order to treat aneurysms, or alternatively, to occlude the blood vessel at a particular location. Many of these systems, depending on the particular location and geometry of the aneurysm, have been used to treat aneurysms with various levels of success. One drawback associated with the use of bare embolization coils relates to the inability to adequately pack or fill the aneurysm due to the geometry of the coils which can lead to long term recanalization of the aneurysm with increased risk of rupture.

Some improvements to bare embolization coils have included the incorporation of expandable foams, bioactive materials and hydrogel technology as described in the following U.S. Pat. No. 6,723,108 to Jones, et al., entitled, "Foam Matrix Embolization Device", U.S. Pat. No. 6,423,085 to Murayama, et al., entitled, "Biodegradable Polymer Coils for Intraluminal Implants" and U.S. Pat. No. 6,238,403 to Greene, et al., entitled, "Filamentous Embolic Device with Expansible Elements." While some of these improved embolization coils have been moderately successful in preventing or reducing the rupture and re-rupture rate of some aneurysms, the devices have their own drawbacks. For instance, in the case of bioactive coils, the materials eliciting the biological healing response are somewhat difficult to integrate with the coil structure or have mechanical properties incompatible with those of the coil making the devices difficult to accurately position within the aneurysm. In the case of some expandable foam and hydrogel technology, the expansion of the foam or hydrogel is accomplished due to an interaction of the foam or hydrogel with the surrounding blood environment. This expansion may be immediate or time delayed but is generally, at some point, out of the control of the physician. With a time delayed response the physician may find that coils which were initially placed accurately and detached become dislodged during the expansion process leading to subsequent complications.

For many aneurysms, such as wide necked or fusiform aneurysms the geometry is not suitable for coiling alone. To somewhat expand the use of embolization coils in treating some wide necked aneurysms, stent like scaffolds have been developed to provide support for coils. These types of stent like scaffolds for use in the treatment of aneurysms have been described in U.S. Pat. No. 6,605,111 to Bose et al., entitled, "Endovascular Thin Film Devices and Methods for Treating Strokes" and U.S. Pat. No. 6,673,106 to Mitelberg, et al., entitled, "Intravascular Stent Device". While these stent like devices have broadened the types of aneurysms amenable to embolization therapy, utilization of these devices in conjunction with embolization devices is technically more complex for the physician, may involve more risk to the patient and have a substantial cost increase for the healthcare system.

To further expand the types of aneurysm suitable for interventional radiological treatment, improved stent like devices have been disclosed in U.S. Pat. No. 5,824,053 to Khosravi et al., entitled, "Helical Mesh Endoprosthesis and Method", U.S. Pat. No. 5,951,599 to McCrory, entitled, "Occlusion System for the Endovascular Treatment of and Aneurysm" and U.S. Pat. No. 6,063,111 to Hieshima et al., entitled, "Stent Aneurysm Treatment System and Method." When placed across the neck of an aneurysm the proposed stent like devices purport to have a sufficient density through the wall of the device to reduce flow in the aneurysm allowing the aneurysm to clot, while at the same time having a low enough density through the wall to allow small perforator vessels adjacent to the aneurysm to remain patent. Stent devices of this nature while having the potential to reduce treatment costs have not been realized commercially due to the difficulty in manufacturing, reliability in delivering the devices to the treatment site and an inability to properly position the denser portion of the stent device accurately over the neck of the aneurysm.

Another cerebrovascular disease state is ischemia resulting from reduced or blocked arterial blood flow. The arterial blockage may be due to thrombus, plaque, foreign objects or a combination thereof. Generally, plaque buildup within the lumen of the vessel, known as atherosclerotic disease, is not generally responsive to thrombolytics or mechanical disruption using guidewires. The approach to the treatment of neurovascular atherosclerotic disease has been to use modified technology developed for the treatment of cardiovascular atherosclerotic disease, such as balloons and stents, to expand the vessel at the site of the lesion to re-establish blood flow. For instance, U.S. Pat. No. 4,768,507 to Fischell et al., entitled, "Intravascular Stent and Percutaneous Insertion Catheter System for the Dilation of an Arterial Stenosis and the Prevention of Arterial Restenosis" discloses a system used for placing a coil spring stent into a vessel for the purposes of enhancing luminal dilation, preventing arterial restenosis and preventing vessel blockage resulting from intimal dissection following balloon and other methods of angioplasty. The coil spring stent is placed into spiral grooves on an insertion catheter. A back groove of the insertion catheter contains the most proximal coil of the coil spring stent which is prevented from springing radially outward by a flange. The coil spring stent is deployed when an outer cylinder is moved proximally allowing the stent to expand. Other stent systems include those disclosed in U.S. Pat. No. 4,512,338 to Balko, et al., entitled, "Process for Restoring Patency to Body Vessels", U.S. Pat. No. 5,354,309 to Schnepp Pesch et al., entitled, "Apparatus for Widening a Body Cavity" and U.S. Pat. No. 6,833,003 to Jones et al., entitled, "Expandable Stent and Delivery System". While the aforementioned devices may have the ability to access the cerebrovasculature, they lack sufficient structural coverage of the lesion to achieve the desired patency of the vessel without the use of a balloon device.

SUMMARY OF THE INVENTION

In accordance with one aspect of the present invention there is provided a medical device deployment system for depositing a medical device within a body lumen of a mammal. The medical device deployment system includes a stent device, a delivery catheter and an inflation source member. The delivery catheter includes a longitudinally extending balloon member coupled to its distal end which is everted and positioned within the catheter lumen. The stent device is positioned at the distal end of the delivery catheter and disposed within the lumen of the catheter within the everted balloon member.

The balloon member of the delivery catheter is typically formed of a thin walled polymeric tube in which the distal end of the tube has been sealed and the proximal end of the balloon member is coupled to the distal end of the catheter in which the lumen of the catheter is in fluid communication with the interior surface of the balloon. The balloon member is preferably formed of a high strength non-compliant polymeric material such as nylon, polyester and others, however, metallic materials such as thin-film nitinol or other alloys may also be suitable.

The stent device preferably takes the form of a helically wound wire or strip primary backbone having multiple adjacent turns where the backbone has side extension members that are spaced apart along the length and extend outwardly from the backbone, generally in the direction of adjacent turns. The side extension members generally have two ends where one end is fixedly coupled to the backbone and the other end extending from the backbone is free, meaning it is typically uncoupled to any other structural member. As the backbone takes successive helical turns, the side extension members may be positioned adjacent to or overlap the side extension members or backbone of subsequent or previous helical turns, generally forming a tubular structure. The overlapping side extension members create a lattice work of apertures between turns of the backbone. The size and distribution of the apertures is a function of the diameter, length and shape of the side extension members and the distance between turns of the backbone. The stent device is formed of a resilient material and has a first constrained elongate tubular configuration for delivery to a target site within a body lumen and a second unconstrained expanded tubular configuration for deployment at the target site.

The inflation source member is coupled to the proximal end of the catheter and used to apply fluid pressure to the lumen of catheter at a level sufficient to cause the balloon member to extend longitudinally from the catheter lumen, thus deploying the stent. The preferred fluids include liquids such as saline although gases such as carbon dioxide gas may be suitable for some system configurations. The amount of fluid pressure required to inflate the balloon is in part related to the increased friction force between the balloon inner surface and the interior wall of the catheter lumen due to the outward force applied by the constrained stent device. The inflation source member preferably takes the form of a syringe (threaded or non threaded), however other inflation sources such as a pressurized fluid source having a valve assembly or a controllable fluid delivery pump are also suitable.

In accordance with another aspect of the present invention there is provided a medical device deployment system. The medical device deployment system includes a stent device, a delivery catheter and an inflation source member. The delivery catheter includes a longitudinally extending balloon member coupled to its distal end which is everted and positioned within the catheter lumen. The stent device is positioned at the distal end of the delivery catheter and disposed within the lumen of the catheter within the everted balloon member. The delivery catheter further includes a flow restriction member positioned within the catheter lumen proximal to the everted balloon and stent. The flow restriction member is preferably formed as tubular member having lumen substantially smaller than the lumen of the catheter. The flow restriction member may be formed of a metal, ceramic, polymer or any mixture thereof and have dimensional characteristics that do not significantly impact the ability of the catheter to access target sites within the vasculature. The flow restriction member performs the function of limiting the flow of fluid delivered from the proximal end of the catheter to the everted balloon member during deployment. This flow restriction member allows the balloon member to evert during inflation (while advancing the stent device) in a more controlled manner. As the fluid pressure applied to the lumen of the catheter reaches a sufficient level, the fluid pressure causes the balloon to begin to deploy, subsequently advancing the stent. Once sufficient pressure is applied, the rate at which the balloon can deploy longitudinally from the catheter is dependent upon the volume of fluid available to inflate the balloon volume. The flow restriction member prevents the balloon member from inflating too rapidly (and uncontrollably deploying the stent) by reducing the volume of fluid available for inflation thus providing more control over how the stent is deployed.

In accordance with yet another aspect of the present invention there is provided a stent device having a backbone and side extension members which may take various configurations comprising any of the following: side extension members on each side of the backbone which are uniformly spaced along the length of the backbone; side extension members on each side of the backbone which are not uniformly spaced along the length of the backbone; side extension members having a curved shape; side extension members having a straight shape; side extension members extending from the backbone in an angled direction; side extension members having different lengths; side extension members having apertures; side extension members having radio-opaque markers; side extensions having an enlarged tabular end; backbones having apertures; backbones having radio-opaque marker(s); backbones having a curvilinear or Z shape.

In accordance with still another aspect of the present invention there is provided a method of reconstructing a body lumen having a defect using a stent device according to an embodiment of the present invention. The method comprises the steps of: positioning a stent device deployment system within a vessel adjacent a target site; applying fluid pressure to the interior lumen of the catheter; extending the balloon member from the catheter lumen longitudinally, thereby allowing a portion of the stent to be deployed adjacent the target site; retracting the catheter relative to the deployed portion of the stent; controlling the amount of overlap of the side extension members of the stent device during deployment of the stent adjacent the target site; releasing the stent device from the delivery catheter lumen; and releasing the stent from the balloon member.

In accordance with still yet another aspect of the present invention there is provided a stent device wherein the primary helical member is formed of a resilient non-absorbable non-erodible material and a plurality of the extension members are formed of an absorbable or bio-erodible material.

In accordance with still yet another aspect of the present invention there is provided a stent device wherein the primary helical member is formed of a resilient material and includes an absorbable and or erodible material and a plurality of the extension members are formed of a resilient material and includes an absorbable and or erodible material.

In accordance with yet still another aspect of the present invention there is provided a reconstruction device comprising a biocompatible material. Suitable resilient materials include metal alloys such as Nitinol (NiTi), titanium, chromium alloy, stainless steel. Additional materials include polymers such as polyolefins, polyimides, polyamides, fluoropolymers, polyetheretherketone (PEEK), cross-linked PVA hydrogel, polytetrafluoroethylene (PTFE), expanded polytetrafluoroethylene (ePTFE), porous high density polyethylene (HDPE), polyurethane, and polyethylene terephthalate, or biodegradable materials such as polylactide polymers and polyglycolide polymers or copolymers thereof and shape memory polymers. The medical device may comprise numerous materials depending on the intended function of the device. These materials may be formed into desired shapes or attached to the device by a variety of methods which are appropriate to the materials being utilized such as laser cutting, injection molding, spray coating and casting.

In accordance with another aspect of the present invention there is provided a reconstruction device having a coating formed of a biocompatible, bioerodible and biodegradable synthetic material. The coating may further comprise one or more pharmaceutical substances or drug compositions for delivering to the tissues adjacent to the site of implantation, and one or more ligands, such as peptides which bind to cell surface receptors, small and/or large molecules, and/or antibodies or combinations thereof for capturing and immobilizing, in particular progenitor endothelial cells on the blood contacting surface of the medical device.

DETAILED DESCRIPTION OF THE INVENTION

Figure 1:
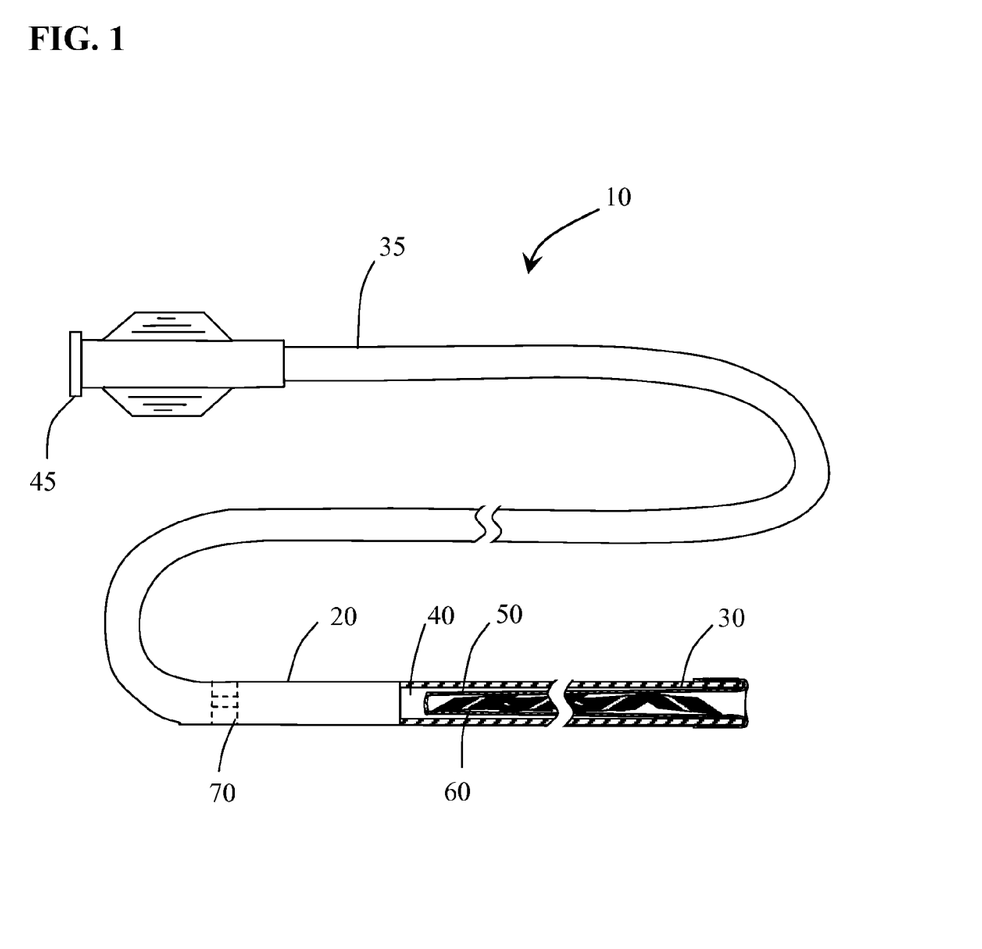
FIG. 1 is a partial cross-sectional of a stent deployment system according to an embodiment of the present invention.

Methods and systems for performing vascular reconstruction and revascularization in a desired area of the body are herein described. FIG. 1 illustrates a medical device deployment system 10 suitable for use with embodiments of the present invention. Deployment system 10 includes an elongate tubular catheter 20 having distal and proximal ends 30 and 35 respectively and a through lumen 40 providing fluid communication between the catheter proximal hub 45 and balloon 50 which is everted and positioned within lumen 40 at distal end 30. While catheter 20 is shown having a single lumen 40 it should be understood that catheter 20 may incorporate additional lumens as needed. For instance catheter 20 may be formed from a dual lumen extrusion in which one lumen is used for coupling to balloon 50 and the second lumen to facilitate use of a guidewire for navigating the catheter to a target site. Alternatively, the second lumen may not extend the full length of the catheter and may only be positioned at the catheters distal end for use in a rapid exchange manner. Stent 60 is positioned within catheter lumen 40 inside of everted balloon 50. Positioned within catheter lumen 40 proximal to balloon 50 is flow restriction member 70.

Figure 2A:
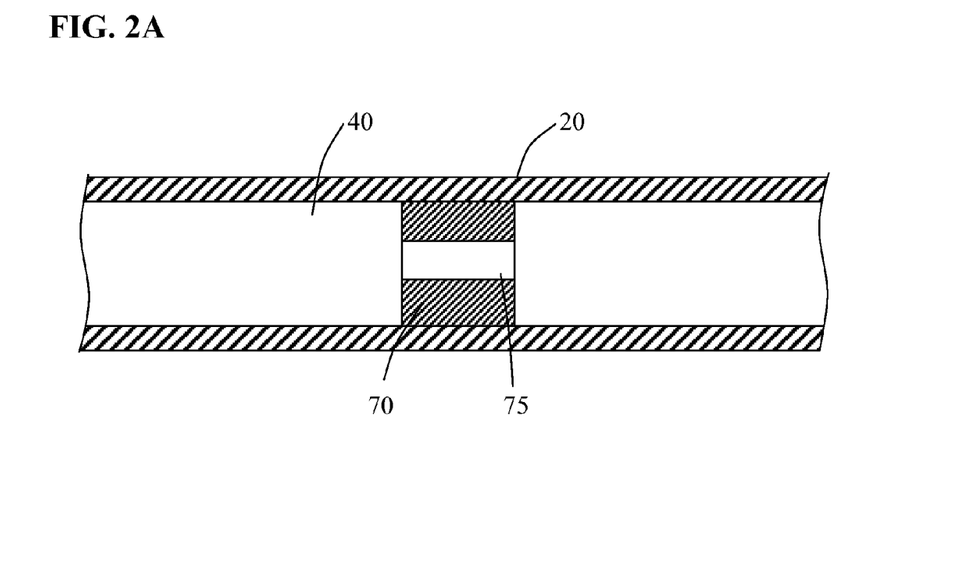
FIGS. 2A and 2B are enlarged partial cross-sectional views of the distal end of the stent deployment system according to an embodiment of the present invention.
Figure 2B:
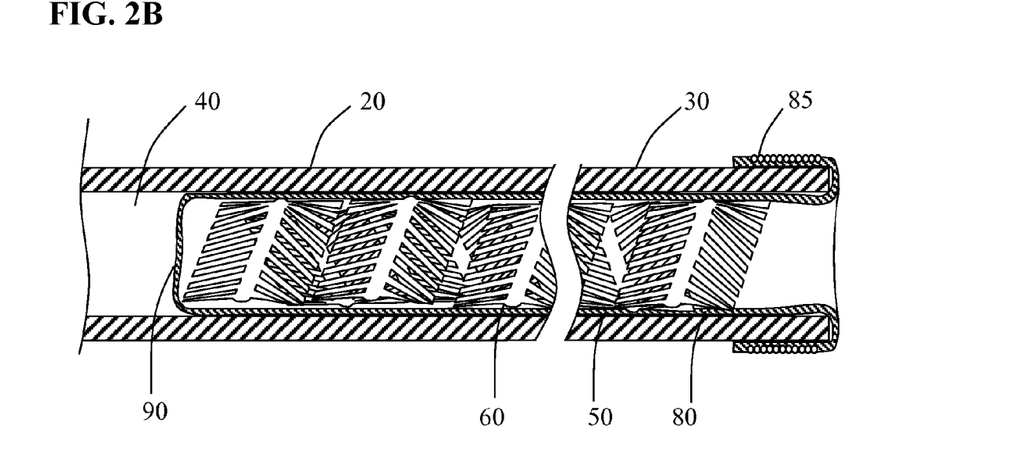

FIG. 2A depicts a magnified partial cross-sectional view of catheter 20 proximal to balloon 50. While not shown, the construction of catheter 20 may utilize known catheter technologies that incorporate braiding and or coiling using metallic or non-metallic reinforcing filamentous materials to provide high strength while maintaining catheter flexibility. The incorporation of lubricious hydrophilic and or hydrophobic materials on the inner and or outer surface of the catheter is considered to be within the scope of known catheter construction techniques and suitable for use in a deployment system of the present invention. Flow restriction member 70 having a through lumen 75 is shown secured to the inner wall of catheter 20. Flow restriction member 70 may be formed of any suitable material including metals, ceramics or polymers and is generally cylindrical matching the general contour of catheter lumen 40. Preferably, flow restriction member 70 is formed of a polymer such as a nylon or polyolefin and may be secured in place using known techniques such as crimping, heat fusing, ultrasonic welding or gluing. The diameter of lumen 75 is in the range of 10% to 90% of catheter lumen 40. FIG. 2B illustrates a magnified partial cross-sectional view of distal end 30 of catheter 20. Balloon 50 is everted and positioned within lumen 40 of catheter 20 such that the inner surface of balloon 50 is fluid communication with lumen 40 and the exterior of the balloon is not in fluid communication with lumen 40. Balloon 50 is preferably formed from an elongate thin walled non-compliant material. Suitable polymeric materials include nylon or polyester tubes having a wall thickness from 0.0001 inches to 0.010 inches with a preferred range of about 0.0005 inches to 0.005 inches. Other suitable materials include metallic thin film alloys such as nitinol having a wall thickness in the range of about 0.0001 inches to about 0.001 inches. Balloons of the present invention typically have a length that is substantially longer than the collapsed implantable devices such as a stent and range from about 40 mm to about 500 mm with a preferred range of about 50 mm to 400 mm. Optionally, balloon members of the present invention may include lubricious hydrophilic and or hydrophobic materials on the inner and or exterior surface of the balloon to reduce friction between the balloon surface and the catheter or the balloon surface and a collapsed device. Balloon member 50 typically has a diameter less than 1.5 times the outer diameter of catheter 20 but preferably has a diameter equal to or smaller than the outer diameter of catheter 20. The balloon proximal end 80 is coupled to distal end 30 and by securing member 85. Securing member 85 is shown as a flexible polymer filament wound around proximal end 80 and catheter distal end 30. Balloon proximal end 80 and distal end 30 may be secured using other means such as heat fusing, ultrasonic welding and or gluing to insure a good bond and seal. The distal end 90 of balloon 50 is completed sealed using any of the aforementioned techniques and positioned within catheter lumen 40 proximal to proximal end 80 of the balloon. Stent device 60 is shown in a compressed helical configuration within the channel defined by the exterior surface of balloon 50 within catheter lumen 40. While stent device 60 is shown as a helical stent it should be understood that alternate self expanding stent configurations such as those described in U.S. Pat. Nos. 6,673,106 and 6,818,013 to Jones et al., entitled, "Intravascular Stent Device", having closed cell construction, U.S. Pat. No. 5,827,321 to Roubin et al., entitled, "Non-Foreshortening Intraluminal Prosthesis", having non-foreshortening characteristics and generally known stents having an open cell configuration are suitable for deployment utilizing a deployment system of the present invention.

Figure 3A:
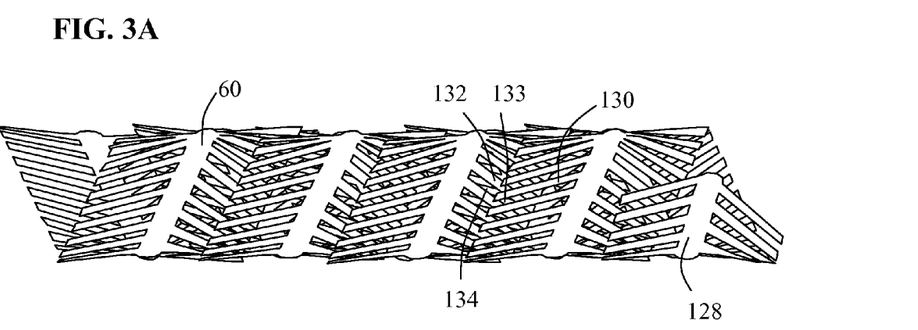
FIG. 3A is a side view of a deployed stent device according to an embodiment of the present invention.
Figure 3B:
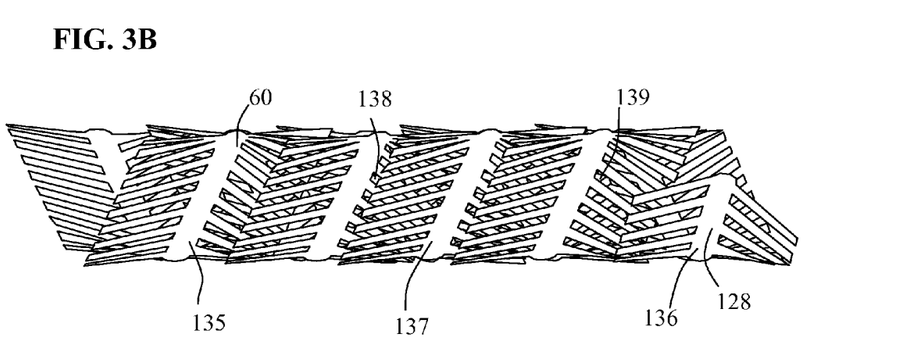
FIG. 3B is a side view of a deployed stent device according to another embodiment of the present invention.

FIG. 3A illustrates detail of stent device 60 in an expanded configuration. The primary backbone 128 is shown in a uniform helical shape along with side extension members 130 and adjacent turn side extension members 132. As depicted, the side extension members of the stent device generally have one end secured to the backbone and the other end uncoupled which is unlike previous stents described in the art. This configuration allows the side extension members of the present invention to act as individual cantilevers providing an improved ability to conform to discrete contours within the vasculature. Alternatively, both ends of the side extension members may be coupled to the primary backbone, forming a looped structure for example, as long as the side extension member is discrete and not fixedly coupled to any other structural member. Prior art helical stents formed of a ladder or mesh structure in which side extension members do not have a free end or are not discrete, such as those described in U.S. Pat. No. 6,660,032 to Klumb et al, entitled, "Expandable Coil Endoluminal Prosthesis" or U.S. Pat. No. 5,824,053 to Koshravi et al, entitled "Helical Mesh Endoprosthesis and Method of Use", do not have the same ability to conform to discrete contours of a lesion within the vasculature and instead form a wide area "tented" surface. Stent device 60 is shown with side extension members 130 partially overlapping adjacent turn side extension members 132. The overlap of these side extension members creates overlap apertures 133 and residual apertures 134. The size, shape and distribution of the overlap apertures 133 and the residual apertures 134 is dependant upon the size shape and distribution of the side extension members 130 and adjacent turn side extension members 132 and the degree of overlap of the adjacent turns defined in part by the pitch of the primary backbone 128. The stent may have a diameter in the range of 1 to 50 mm, and preferably between 2 and 15 mm. The diameters of the side extension members have a range of between 0.0001 and 0.025 inches with a preferred range of between 0.002 to 0.010 inches. The spacing between side extension members range between 0.001 and 0.250 inches with a preferred range between 0.002 and 0.060 inches. FIG. 3B illustrates detail of stent device 60 according to another embodiment of the present invention wherein backbone 128 has a non-uniform helical shape in which the pitch at stent ends 135 and 136 is wider than the pitch towards the stent middle 137. This pitch variation causes the overlap of side extension members near the ends of the stent to be less than the overlap of side extension members towards the middle of the stent. As an outcome of the variable overlap there is a larger number of smaller overlap apertures in the middle of the stent than at the stent ends and the residual aperture 138 adjacent the stent middle 137 is substantially smaller than the residual aperture 139 adjacent the stent ends 135 and 136. The ensuing result is that the stent device 60 has a lower porosity in the stent middle 137 and a higher porosity at the stent ends 135 and 136.

Figure 4A:
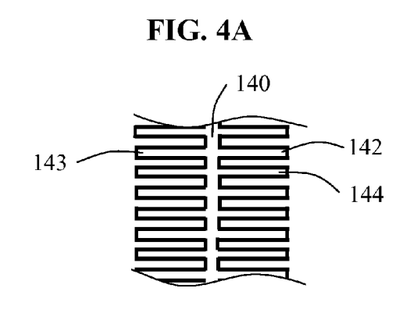
FIGS. 4A through 4L are partial flat pattern views of stent devices according to embodiments of the present invention.
Figure 4B:
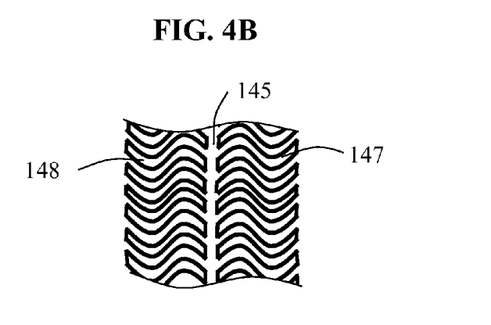
Figure 4C:
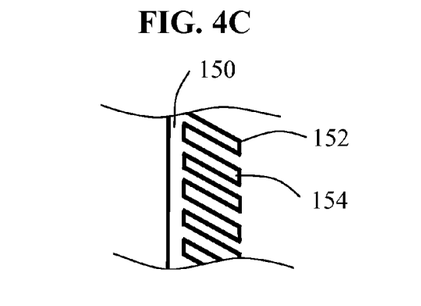
Figure 4D:
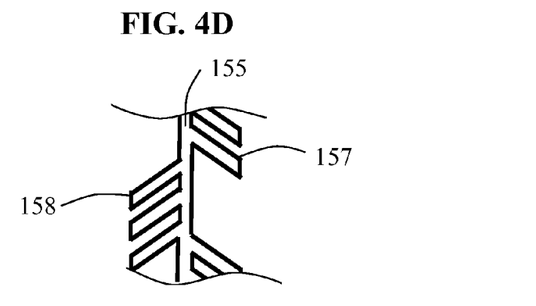
Figure 4E:
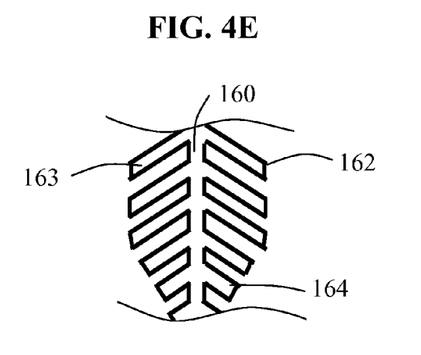
Figure 4F:
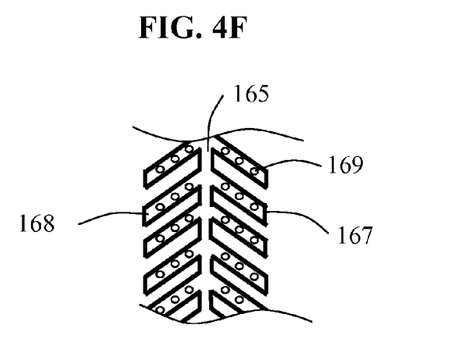
Figure 4G:
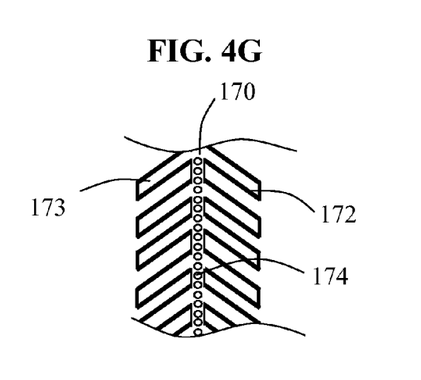
Figure 4H:
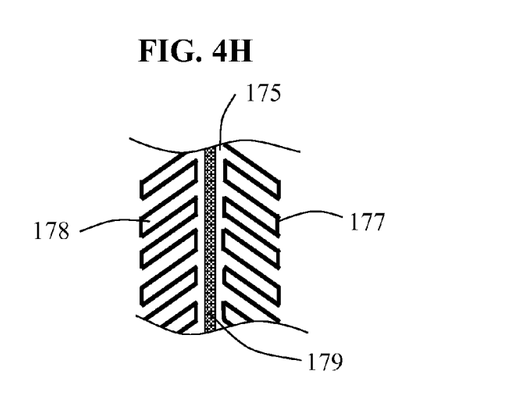
Figure 4I:
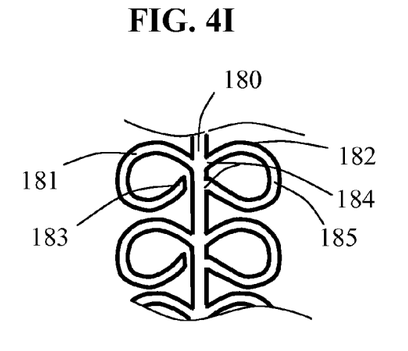
Figure 4J:
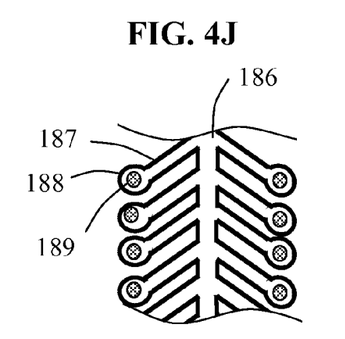
Figure 4K:
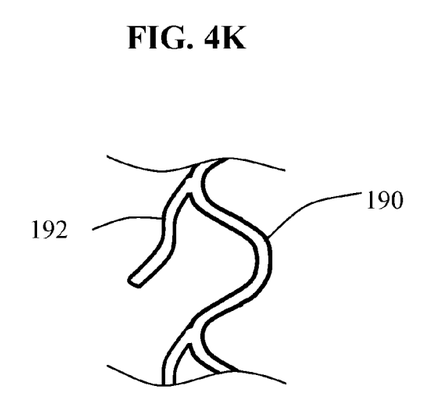
Figure 4L:
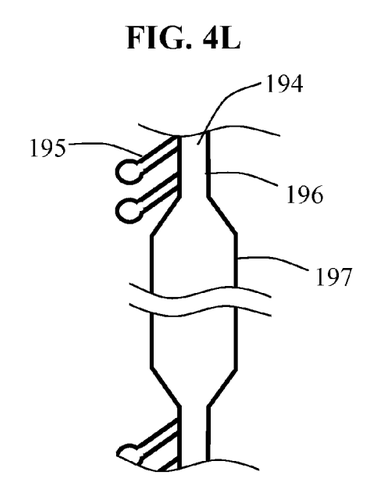
Figure 5A:
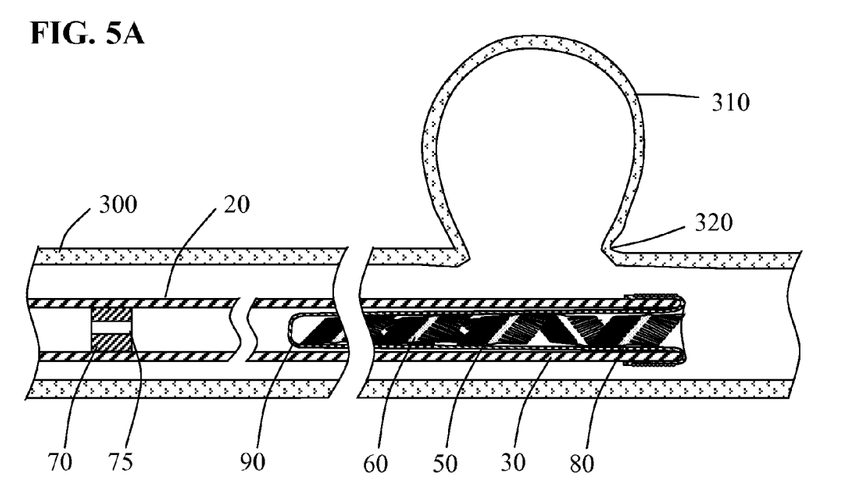
FIGS. 5A through 5D are partial cross-sectional views illustrating a method of deploying a stent device within a vessel at a target site adjacent an aneurysm according to an embodiment of the present invention.
Figure 5B:
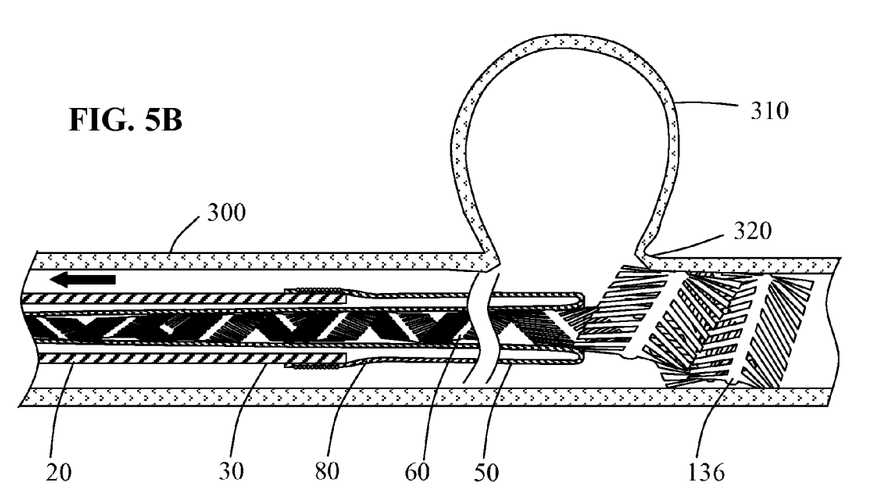
Figure 5C:
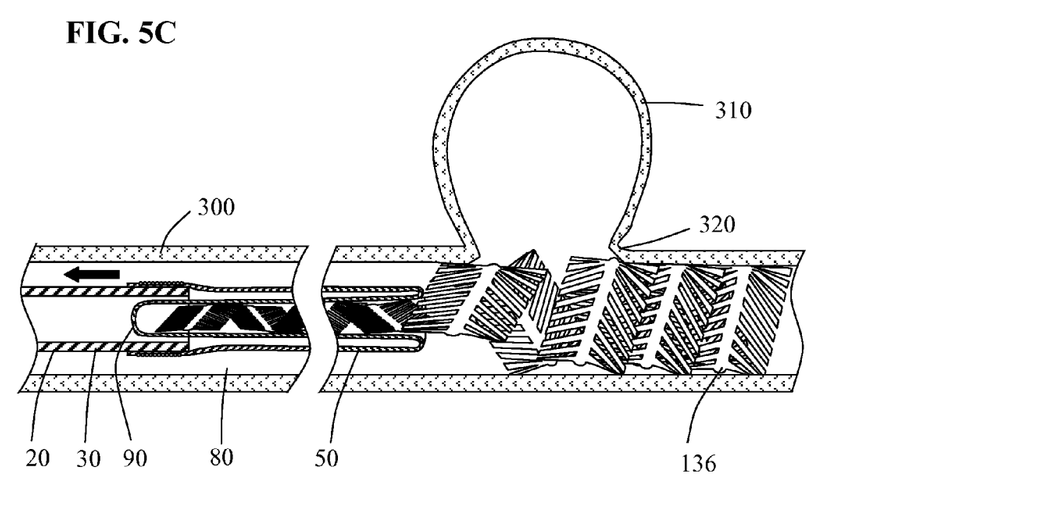
Figure 5D:
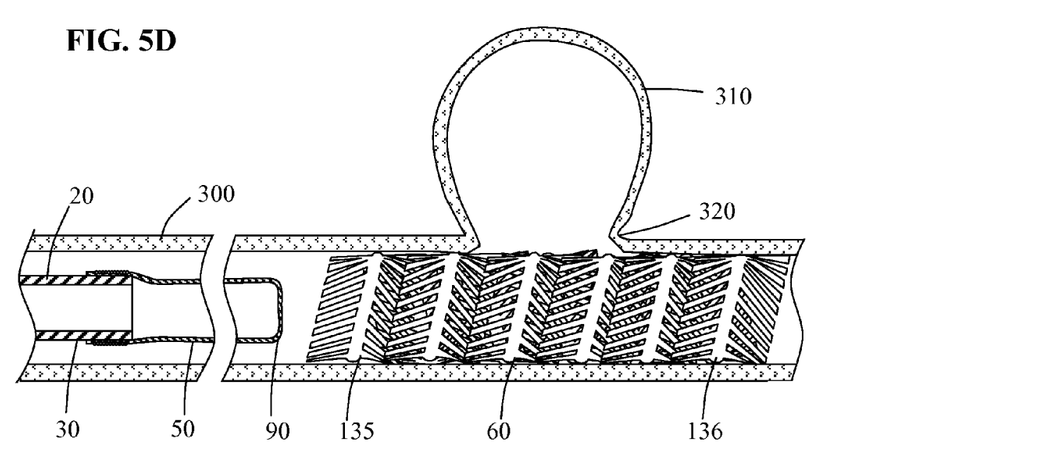

In addition to the pitch of the stent backbone having an influence on the overall porosity and porosity distribution of the stent device there exists numerous variations in the size shape and distribution of side extension members that may also influence porosity. FIGS. 4A through 4E illustrate partial flat patterns of some variations of side extension members relative to a backbone that may affect different aspects of stent performance including porosity and porosity distribution when formed in a helical shape. In one pattern variation shown in FIG. 4A, a stent device has a primary backbone 140 with side extension members 142 and 143, having generally similar diameters and lengths, extending from opposite sides of the backbone 140. Side extension member 144, positioned adjacent extension member 142 has a similar length to extension 142 however may have a smaller width or diameter. The alternating pattern of side extension members having different widths or diameters may be extended along backbone 140. FIG. 4B depicts another pattern variation in which a stent device has a primary backbone 145 and side extension members 147 and 148, with generally similar widths, diameters and lengths extending from opposite sides of backbone 145 in a curvilinear shape. FIG. 4C illustrates another pattern variation in which a stent device has a primary backbone 150 and side extension members 152 and 154 which are positioned on only one side of the backbone 150. FIG. 4D shows still another pattern variation in which a stent device has a primary backbone 155 and groups of side extension members 157 and 158 are positioned in an alternating configuration on opposite sides of the backbone. FIG. 4E depicts still another pattern variation in which a stent device has a primary backbone 160 and side extension members 162 and 163 with generally similar diameters and lengths extending from opposite sides of backbone 160. Additionally, the side extension members may progressively have shorter lengths, such as side extension member 164, to provide a tapered configuration. FIG. 4F illustrates yet still another pattern in which a stent device has a primary backbone 165 and side extension members, 167 and 168 with generally similar diameters and lengths extending from opposite sides of backbone 165. Additionally the side extension members contain apertures 169. FIGS. 4G and 4H illustrate partial flat patterns of some variations of a backbone relative to side extension members that may affect different aspects of stent performance including porosity and porosity distribution as well as radiographic visibility when formed in a helical shape. FIG. 4G depicts a pattern of a stent device that has a primary backbone 170 and side extension members 172 and 173, with generally similar diameters and lengths extending from opposite sides of backbone 170. Along the length of backbone 170 there is a plurality of apertures 174. FIG. 4H depicts a pattern of a stent device that has a primary backbone 175 and side extension members 177 and 178, with generally similar diameters and lengths extending from opposite sides of backbone 175. Along the length of backbone 175 there is a radio-opaque member 179. The radio-opaque member 179 provides fluoroscopic visualization of the stent during the deployment procedure. For a stent device having an expanded diameter and a pre-set initial overlap of side extension members upon each helical turn of the backbone, the radio-opaque member 179 provides a visual indication of the stent pitch. As the spacing between adjacent turns of radio-opaque member 179 decreases, the amount of side extension member overlap with adjacent turns increases. FIG. 4I depicts yet another pattern of a stent device that has a primary backbone 180 and a plurality of side extension members represented by side extension members 181 and 182. Side extension members 181 and 182 are positioned on opposite sides of backbone 180 in a generally mirrored fashion for this configuration. Side extension members 181 generally take the form of an open ended loop, where a first end of the extension member loop is connected to the backbone and the second end 183 is adjacent the backbone but are not connected. Side extension members 182 generally take the form of a closed loop, where two ends 184 of the extension member loop are connected to backbone 180. As can be appreciated, side extension members 182 form a discrete side unit where it is unconnected to other side extension members except through the backbone 180. From a broader perspective two ends 184 may be considered as a first end region coupled to the backbone and a second end region 185, as shown, is free or uncoupled to any other structural member. While these loops are shown generally "circular", the size and shape of the loop may take the form of other geometric shapes and patterns to be commensurate with the desired properties of the formed stent. For instance the loops may be rectangular, triangular or form a flattened spiral. FIG. 4J illustrates another pattern of a stent device according to an embodiment of the present invention that has a primary backbone 186 and a representative side extension member 187. While a first end of side extension member 187 is integrally coupled to backbone 186, the second end of the side extension member is uncoupled to the backbone and takes the form of an enlarged tabular end 188. This tabular end 188 is preferably rounded as to be atraumatic to the vessel wall and may include a marker element 189. Preferably marker element 189 is radio-opaque for use in fluoroscopy using known materials such as gold, platinum, tantalum, tungsten, etc., however marker materials suitable for direct visual or magnetic resonance imaging are also contemplated. Marker element 189 may be formed using coining techniques in which a round marker is press fit into a slightly smaller opening positioned on tabular end 188. Alternatively, marker 189 may be printed, coated, electro-deposited, riveted, glued, recessed or raised relative to tabular end 188. More broadly, an entire stent device or portion thereof may be coated with a radio-opaque material to provide visibility under fluoroscopy. While the marker shown in FIG. 4J is positioned at tabular end 188, the marker may be positioned at any location on the side extension member. For instance the side extension member may take the form of a threaded member and a marker take the form of a coil that is wound over the side extension member. FIG. 4K depicts still yet another flat pattern of a stent device in which the backbone 190 takes a curvilinear shape. For representative simplicity, backbone 190 is shown as being somewhat sinusoidal. Side extension member 192, also shown to be curvilinear, extends from a peak on backbone 190. As can be appreciated, side extension members such as side extension member 192 may extend from different locations on backbone 190. FIG. 4L illustrates a stent pattern where backbone 194 has side extension members represented by side extension member 195. Along its length, backbone 194 has a first width 196 and a second width 197. To impart some stretch resistance for the finished stent width 197 is shown to be greater than width 196. The amount of stretch resistance imparted in the finished stent is related to the relative difference between the two widths. The larger width may range from 1.01 to 100 times the width of the smaller width with a preferable range of 1.5 to 20 times. While FIG. 4L shows two such differing widths of the backbone, a stent may have multiple regions of differing width to make the stent suitable for a particular anatomy and clinical application. As with any of the aforementioned stent device pattern variations, these patterns may extend along the entire length of the backbone or only a portion thereof and in some instances features of various patterns may be provided in a combined fashion to form stent devices having unique performance characteristics. Preferably, stent devices of the present invention comprise a biocompatible resilient material. Suitable resilient materials include metal alloys such as nitinol, titanium, stainless steel. Additional suitable materials include polymers such as polyimides, polyamides, fluoropolymers, polyetheretherketone (PEEK) and shape memory polymers. As can be appreciated, embodiments of stent devices of the present invention may be formed in part or entirely of bioabsorbable and or bioerodible materials such as polycaprolactone (PCL), polyglycolic acid (PGA), polydioxanone (PDO) and combinations thereof to allow the stent to temporarily serve structural clinical applications, deliver pharmacological compounds and then dissolve over time. These materials may be formed into desired shapes by a variety of methods which are appropriate to the materials being utilized such as laser cutting, thermal heat treating, vacuum deposition, electro-deposition, vapor deposition, chemical etching, photo-chemical etching, electro etching, stamping, injection molding, casting or any combination thereof. Preferably the stent backbone and the side extension members are integrally formed. The distance a side extension member extends from the backbone is dependant upon a specific stent design but a typical range includes between 0.5 to 100 times the width of the backbone and a preferred range being about 0.75 to 25 times the backbone width. The backbone widths have a general range of about 0.0005 in to 0.250 in with a preferred range of about 0.001 in to 0.100 in. While various configurations of side extension members, backbones and a discussion of pitch have been provided, the features of a particular stent design features are heavily dependant upon the clinical application and location of the stent. For instance, stents placed in vessels known to exhibit substantial pulsatility may require that the stent be designed to have end regions which are larger in diameter than the middle portion of the stent to better anchor the stent at the target location. Additionally, the width of the backbone may vary to provide regions of the stent which are less susceptible to elongation, thereby creating a stent that has localized stretch resistant properties which aids in reducing stent migration. Stents sufficient for treating an aneurysm without the aid of other embolization devices positioned within the aneurysm may require that the porosity of the deployed stent in the region of the aneurysm neck be less than about 30 percent. Additionally, stents for treating aneurysm in certain locations may require that the porosity across the neck be less than 30 percent however the porosity adjacent either side of the aneurysm neck be greater than 40 percent and have dimensions as not to occlude small perforator vessels adjacent the aneurysm neck. Stents used to treat fusiform aneurysms may be considerably longer than stents for berry aneurysms. Stents for use in treating a stenotic lesion may require more or less than 50 percent porosity however side member geometry should be designed to keep fragmented plaque trapped between the exterior wall of the stent and interior wall of the vessel.

As previously discussed, a specific stent device design is heavily dependant upon the clinical application for the device and may include materials or coatings to improve the biocompatibility of the device such as coatings that include ligands adapted to capture endothelial progenitor cells within the vasculature. Additionally, the stent device may include portions of the device such as side extension members which are formed of bio-erodible or bio-absorbable materials and or materials suitable for the delivery of pharmacological or therapeutic agents adapted to encourage healing during the treatment of aneurysms or reduction of plaque or restenosis during the treatment atherosclerotic lesions. Materials and coating process technology suitable for application to the present invention are described in U.S. Patent Application Publication No: 20070128723 A1 to Cottone et al., entitled, "Progenitor Endothelial Cell Capturing with a Drug Eluting Implantable Medical Device" herein incorporated by reference in its entirety.

FIGS. 5A through 5D illustrate a method of deploying a stent device adjacent a vascular defect according to one embodiment of the present invention. The deployment system 10 is positioned within a target vessel 300 having a bulging vascular defect known as an aneurysm 310. The interior of the aneurysm is coupled to the lumen of the vessel at aneurysm neck 320. The catheter distal end 30 including a stent device 60 is positioned adjacent aneurysm neck 320. Stent device 60, being in its first constrained configuration for delivery, is positioned within everted balloon 50 within catheter lumen 40 at catheter distal end 30. A fluid source member such as a syringe (a fluid delivery pump or pressurized fluid source may also be suitable) is coupled to proximal end 35 of catheter 20 at hub 45. As sufficient fluid pressure is applied to lumen 40 of the catheter, balloon 50 begins to inflate and extend distally thereby advancing stent 60 distally. As balloon 50 extends longitudinally, catheter 20 is retracted as a portion of stent device 60 exits the distal end of the catheter and the confines of balloon 50 to move from its first constrained configuration to its second expanded configuration where the distal end 136 of stent device 60 contacts the inner wall of vessel 300. As discussed previously, catheter 20 preferably includes a flow restrictor member that aids in controllably deploying stent device 60. During the deployment process the physician has the ability to control the placement of helical winds of the stent device through advancement of the stent by inflation and retraction of the catheter to obtain the desired overlap of side extension members. This process of modifying the overlap amount gives the physician the ability to increase or decrease the porosity of the stent device 60 as needed for a particular target deployment location. Deployment of stent 60 is complete after the proximal end 135 has been deposited in the target vessel. The balloon 50 may be deflated and catheter 20 removed from the patient.

Figure 6A:
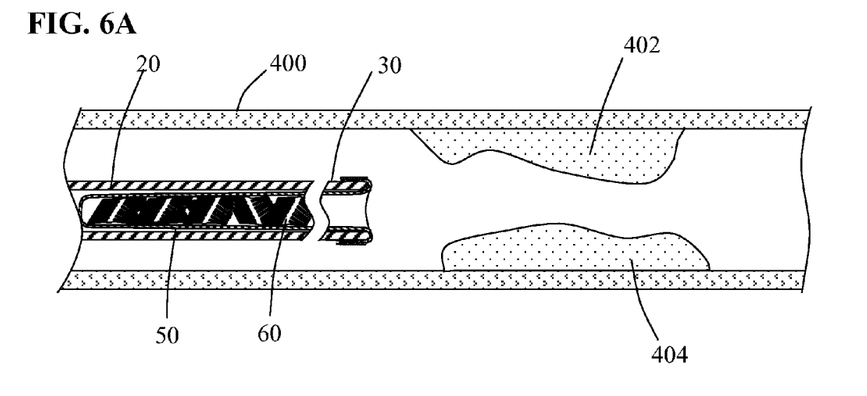
FIGS. 6A through 6D are partial cross-sectional views illustrating a method of deploying a stent device within a vessel at a target site adjacent an atherosclerotic lesion according to an embodiment of the present invention.
Figure 6B:
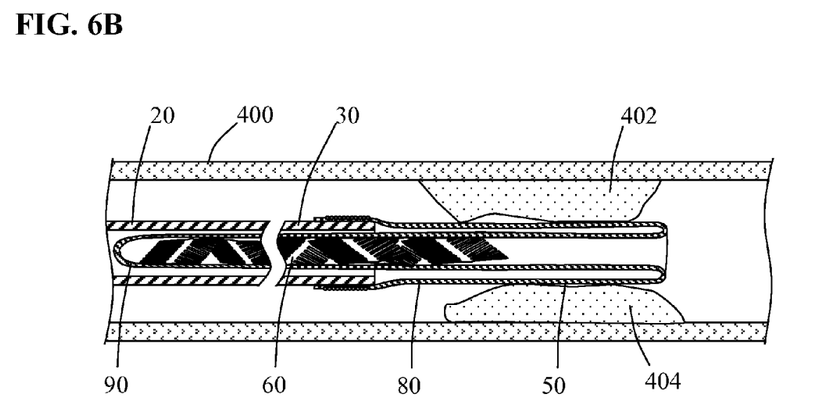
Figure 6C:
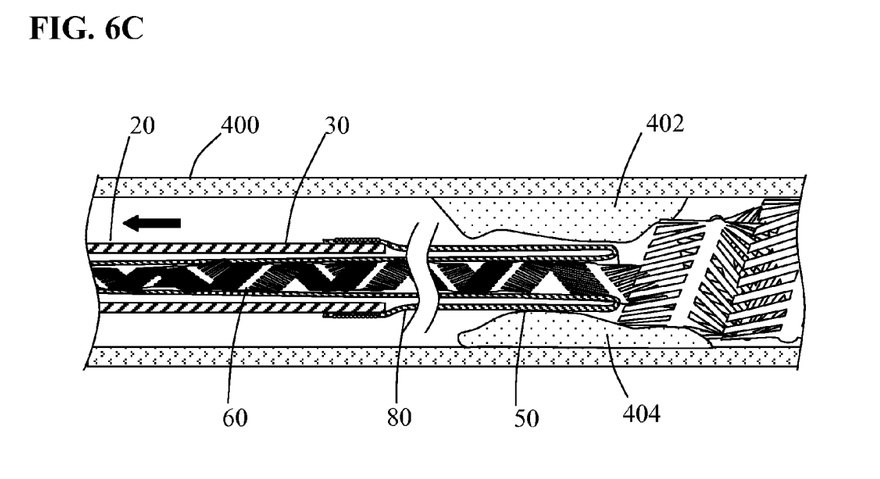
Figure 6D:
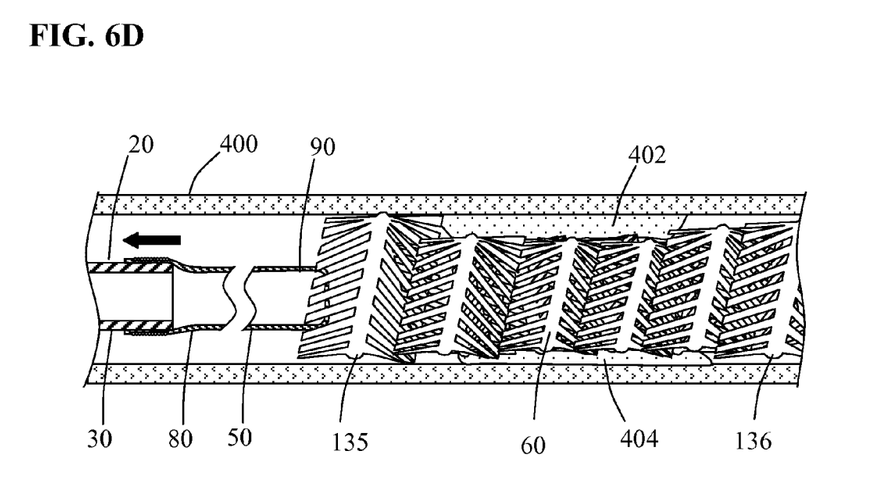

FIGS. 6A through 6D illustrate a method of deploying a stent device adjacent a vascular defect according to another embodiment of the present invention. The deployment system is positioned within a target vessel 400 having an atherosclerotic lesion comprising plaque deposits 402 and 404 creating a stenosis within the vessel restricting distal blood flow. The catheter distal end 30 including a stent device 20 is positioned adjacent plaque deposits 402 and 404. Stent device 60, being in its first constrained configuration for delivery, is positioned within everted balloon 50 within catheter lumen 40 at catheter distal end 30. A fluid source member such as a syringe (a fluid delivery pump or pressurized fluid source may also be suitable) is coupled to proximal end 35 of catheter 20 at hub 45. As sufficient fluid pressure is applied to lumen 40 of the catheter, balloon 50 begins to inflate and extend distally thereby advancing stent 60 distally. FIG. 6B illustrates the inflation and longitudinal extension of balloon 50 such that the balloon 50 partially crosses the lesion prior to stent device 60 fully exiting catheter lumen 40. As balloon 50 extends longitudinally catheter 20 is retracted a portion of stent device 60 exits the distal end of the catheter and the confines of the balloon 50 to move from its first constrained configuration to its second expanded configuration where the distal end 136 of stent device 60 contacts the inner wall of vessel 400 distal to the lesion. As discussed previously, catheter 20 preferably includes a flow restrictor member that aids in controllably deploying stent device 60. During the deployment process the physician has the ability to control the placement of helical winds of the stent device through advancement of the stent by inflation and retraction of the catheter to obtain the desired overlap of side extension members. This process of modifying the overlap amount gives the physician the ability to increase or decrease the porosity of the stent device 60 as needed for a particular target deployment location. Further retraction of catheter distal end 30 relative to the deployed stent portion allows more of stent device 60 to be deployed in a helical overlapping fashion contacting the plaque deposits 402 and 404. Deployment of stent device 60 is completed when the last portion of the stent device exits the lumen of catheter distal end 30 and all of stent device 60 is in its second expanded configuration spanning the lesions. Although stent device 60 is in the second expanded deployment configuration stent device 60 has a normal unconstrained diameter which is larger than the second expanded configuration and thusly the inner diameter of vessel 400. The resilient nature of stent device 60, being in an expanded configuration and slightly constrained by the lesion and vessel, creates chronic outward force which is applied to plaque deposits 402 and 404 as well as vessel 400. The chronic outward of force applied by the stent device 60 is a result of many different design attributes of the stent including the dimensions and geometry of the backbone, the phase transformation temperature, Af, of the nitinol used and the shape set normal unconstrained expanded diameter of the stent. When properly designed, the chronic outward force of stent device 60 allows the gradual expansion of the stent diameter in the vicinity of the plaque deposits 402 and 404 to thereby compress the plaque deposits thus reducing the restriction to blood flow in the region. Alternatively, a balloon device may be positioned within the lumen of the deployed stent device 60 and inflated to accelerate the compression of plaque deposit thereby permitting immediate revascularization.

Novel devices, systems and methods have been disclosed to perform vascular reconstruction and revascularization procedures within a mammal. Although preferred embodiments of the invention have been described, it should be understood that various modifications including the substitution of elements or components which perform substantially the same function in the same way to achieve substantially the same result may be made by those skilled in the art without departing from the scope of the claims which follow.

What is claimed is:

1. A stent and deployment system comprising:
   an elongate catheter defining a longitudinal axis having proximal and distal ends and a lumen extending therethrough;
   an elongate tubular balloon having an interior surface, an exterior surface, a proximal and a distal end wherein said proximal end is coupled to the distal end of said catheter and the distal end of said balloon is sealed, said balloon being everted and positioned within the lumen of said catheter whereby the distal end of said balloon is proximal to the proximal end of said balloon, said interior surface being in fluid communication with said catheter lumen and said exterior surface defining a pathway that is not in fluid communication with said catheter lumen;
   a stent device formed of a resilient material and being operable between a first configuration that is compressed and constrained when positioned within said catheter lumen and a second configuration that is expanded when deployed at a target site, said stent device being positioned within said pathway in said first configuration, said stent device includes a primary member having a helical shape with multiple adjacent turns and a plurality of side extension members positioned along the length and extend from said primary member in a general direction of said turns to thereby form a tubular framework, each side extension member having first and second ends wherein one of said first and second ends is fixedly coupled to said primary member and the other end is uncoupled to the primary member of said stent device and said side extension members are only fixedly coupled to each other through said primary member;
   an inflation source member coupled to the proximal end of said catheter for applying fluid pressure to the catheter lumen to thereby cause said everted balloon to extend distally from said catheter lumen and move said stent device from a first position within said catheter lumen to a second position distal to said catheter distal end.

2. A stent and deployment system according to claim 1 wherein said side extension members on a first turn of said primary member, overlap the side extension members on a second turn of said of said primary member.

3. A stent and deployment system according to claim 1 wherein said side extension members on a first turn of said primary member, overlap a second turn of said primary member.

4. A stent and deployment system according to claim 1 wherein said side extension members on a first turn of said primary member, are adjacent the side extension members on a second turn of said of said primary member.

5. A stent and deployment system according to claim 1 wherein said side extension members on a first turn of said primary member, are adjacent a second turn of said primary member.

6. A medical device deployment system comprising:
   an elongate catheter defining a longitudinal axis having proximal and distal ends and a lumen extending therethrough;
   an elongate tubular balloon having an interior surface, an exterior surface, a proximal and a distal end wherein said proximal end is coupled to the distal end of said catheter and the distal end of said balloon is sealed, said balloon being everted and positioned within the lumen of said catheter whereby the distal end of said balloon is proximal to the proximal end of said balloon, said interior surface being in fluid communication with said catheter lumen and said exterior surface defining a pathway that is not in fluid communication with said catheter lumen;
   a stent device formed of a resilient material and being operable between a first configuration that is compressed and constrained when positioned within said catheter lumen and a second configuration that is expanded when deployed at a target site, said stent device including a primary member having a helical shape and a plurality of side extension members, each side extension member having first and second ends wherein one of said first and second ends is fixedly coupled to said primary member and the other end is uncoupled to the primary member of said stent device and said side extension members are only fixedly coupled to each other through said primary member, said stent device being positioned within said pathway in said first configuration;
   an inflation source member coupled to the proximal end of said catheter for applying fluid pressure to the catheter lumen to thereby cause said everted balloon to extend distally from said catheter lumen and move said medical device from a first position within said catheter lumen to a second position distal to said catheter distal end;
   a flow restrictor member having distal and proximal ends and a lumen extending therethrough, said flow restrictor member being coupled to said catheter and positioned proximal to and in fluid communication with said balloon, said flow restrictor having a lumen diameter sufficient to limit uncontrolled expansion of said balloon.

7. A medical device deployment system according to claim 6 wherein said side extension members on a first turn of said primary member, overlap the side extension members on a second turn of said of said primary member.

8. A medical device deployment system according to claim 6 wherein said side extension members on a first turn of said primary member, overlap a second turn of said primary member.

9. A medical device deployment system according to claim 6 wherein said side extension members on a first turn of said primary member, are adjacent the side extension members on a second turn of said of said primary member.

10. A method of deploying an implant comprising the steps of:
    positioning a medical device deployment system comprising an elongate catheter defining a longitudinal axis having proximal and distal ends and a lumen extending therethrough;
    an elongate tubular balloon having an interior surface, an exterior surface, a proximal and a distal end wherein said proximal end is coupled to the distal end of said catheter and the distal end of said balloon is sealed, said balloon being everted and positioned within the lumen of said catheter whereby the distal end of said balloon is proximal to the proximal end of said balloon, said interior surface being in fluid communication with said catheter lumen and said exterior surface defining a pathway that is not in fluid communication with said catheter lumen;
    a stent device formed of a resilient material and being operable between a first configuration that is compressed and constrained when positioned within said catheter lumen and a second configuration that is expanded when deployed at a target site, said stent device comprising a primary member having a helical shape with multiple adjacent turns and a plurality of side extension members positioned along the length and extending from said primary member in a general direction of said turns to thereby form a tubular framework, each side extension member having first and second ends wherein one of said first and second ends is fixedly coupled to said primary member and the other end is uncoupled to the primary member of said stent device, said stent device being positioned within said pathway in said first configuration;

an inflation source member coupled to the proximal end of said catheter for applying fluid pressure to the catheter lumen to thereby cause said everted balloon to extend distally from said catheter lumen and move said medical device from a first position within said catheter lumen to a second position distal to said catheter distal end;

a flow restrictor member having distal and proximal ends and a lumen extending therethrough, said flow restrictor member being coupled to said catheter and positioned proximal to and in fluid communication with said balloon, said flow restrictor having a lumen diameter sufficient to limit uncontrolled expansion of said balloon within a body lumen adjacent a target site;

applying fluid pressure to said catheter lumen to extend said balloon and stent device distally;

deploying a portion of said stent device adjacent the target site;

disengaging the stent device from the catheter lumen distal end;

controlling the proximity between the side extension members on one turn of said primary member and the primary member of an adjacent turn of said primary member during the deployment of the stent device adjacent the target site;

disengaging the stent device from said balloon.

* * * * *